(12) United States Patent
Hillebrand et al.

(10) Patent No.: US 10,934,540 B2
(45) Date of Patent: *Mar. 2, 2021

(54) METHOD AND TEST KIT FOR RAPID ISOLATION OF NUCLEIC ACIDS USING ROUGH SURFACES

(71) Applicant: AJ INNUSCREEN GMBH, Berlin (DE)

(72) Inventors: Timo Hillebrand, Hoppegarten (DE); Thorsten Stroh, Berlin (DE)

(73) Assignee: AJ Innuscreen GmbH, Berlin (DE)

( * ) Notice: Subject to any disclaimer, the term of this patent is extended or adjusted under 35 U.S.C. 154(b) by 299 days.

This patent is subject to a terminal disclaimer.

(21) Appl. No.: 15/568,475

(22) PCT Filed: Feb. 26, 2016

(86) PCT No.: PCT/EP2016/054178
§ 371 (c)(1),
(2) Date: Oct. 21, 2017

(87) PCT Pub. No.: WO2016/169677
PCT Pub. Date: Oct. 27, 2016

(65) Prior Publication Data
US 2018/0148712 A1 May 31, 2018

(30) Foreign Application Priority Data

Apr. 23, 2015 (DE) .................... 10 2015 207 481.1
Jun. 19, 2015 (DE) .................... 10 2015 211 393.0
Jun. 19, 2015 (DE) .................... 10 2015 211 394.0

(51) Int. Cl.
| C12N 15/10 | (2006.01) |
| B01L 3/02 | (2006.01) |
| C12Q 1/6806 | (2018.01) |
| G01N 1/40 | (2006.01) |
| G01N 35/10 | (2006.01) |

(52) U.S. Cl.
CPC ........ *C12N 15/1006* (2013.01); *B01L 3/0275* (2013.01); *C12N 15/1013* (2013.01); *C12Q 1/6806* (2013.01); *G01N 1/405* (2013.01); *G01N 35/10* (2013.01); *B01L 2200/023* (2013.01); *B01L 2200/0631* (2013.01); *B01L 2200/0647* (2013.01); *B01L 2300/0854* (2013.01); *B01L 2300/16* (2013.01); *Y10T 436/255* (2015.01); *Y10T 436/25375* (2015.01)

(58) Field of Classification Search
CPC .................... C12N 15/1006; C12N 15/1013
See application file for complete search history.

(56) References Cited

U.S. PATENT DOCUMENTS 5,171,537 A * 12/1992 Wainwright .......... B01L 3/0275
422/514
2007/0281303 A1* 12/2007 Isakson ................ B01L 3/5082
435/6.16

2008/0207889 A1 8/2008 Sprenger-Hasels et al.
2009/0068662 A1 3/2009 Hillebrand
2009/0069555 A1 3/2009 Hillebrand et al.
2010/0222562 A1 9/2010 Hillebrand
2018/0133710 A1 5/2018 Hillebrand et al.

FOREIGN PATENT DOCUMENTS

| DE | 10 2005 053463 A1 | 5/2007 |
| DE | 10 2005 059217 A1 | 6/2007 |
| EP | 1 690 938 A1 | 8/2006 |
| WO | 2001/062976 | 8/2001 |
| WO | 2002/038758 | 5/2002 |

OTHER PUBLICATIONS

Jun, Bong-Hyun et al. "Protein separation and identification using magnetic beads encoded with surface-enhanced Raman spectroscopy." Analytical Biochemistry (2009) 391 24-30. (Year: 2009).*
Holmberg et al. "High-throughput, Automated Extraction of DNA and RNA from Clinical Samples using TruTip Technology on Common Liquid Handling Robots" Journal of Visualized Experiments, 76, pp. 1-10 (Year: 2013).*
Lougheed Genetics Laboratory Manual "DNA extraction protocols" (Year: 2005).*
Andreou "Preparation of Genomic DNA from Bacteria" Methods in Enzymology, vol. 529,pp. 143-151. (Year: 2013).*
Stratagene Catalog, p. 39. (Year: 1988).*
U.S. Appl. No. 15/568,474, filed Oct. 21, 2017, 2018/0133710, Hillebrand et al.
Vogelstein et al. "Preparative and analytical purification of DNA from agarose" Proceedings of the National Academy of Sciences, vol. 76, No. 2; pp. 615-619; Feb. 1, 1979.
International Search Report mailed in PCT/EP2016/054178 dated Jul. 18, 2016, with English language translation.
Written Opinion of the International Searching Authority mailed in PCT/EP2016/054178 dated Jul. 18, 2016, with English language translation.
International Preliminary Report on Patentability mailed in PCT/EP2016/054178 dated Oct. 24, 2017.

* cited by examiner

Primary Examiner — Jezia Riley (74) Attorney, Agent, or Firm — Grüneberg and Myers PLLC (57) ABSTRACT

The invention relates to a method for isolation of nucleic acids from aqueous samples containing nucleic acids in free form or liberated by lysis. Before or after the polarity of the aqueous solution is lowered, the sample is brought into contact with a solid phase that has a rough or structured surface, whereupon the nucleic acids precipitate on the solid phase and then, together with the solid phase, are removed from this aqueous solution. The rough or structured surface is preferably a non-smooth metal, plastic or rubber surface. Subject matter of the invention is also a test kit and a corresponding instrument for isolation of nucleic acids.

15 Claims, 3 Drawing Sheets

METHOD AND TEST KIT FOR RAPID ISOLATION OF NUCLEIC ACIDS USING ROUGH SURFACES

Subject matter of the invention is a completely novel, universal greatly simplified as well as extremely fast method for isolation of nucleic acids from the most diverse starting materials containing nucleic acids, which method not only guarantees very high quality of the nucleic acids to be isolated but also permits isolation of extremely high nucleic acid yields. The method can be performed both manually in the laboratory and under field conditions as well as in a completely automated process. It is based on binding of nucleic acids on a non-smooth surface.

Under traditional conditions, DNA is isolated from cells and tissues by digesting the starting materials containing nucleic acids under strongly denaturing and reducing conditions, sometimes also with use of protein-degrading enzymes, purifying the resulting nucleic acid fractions via phenol/chloroform extraction steps and obtaining the nucleic acids from the aqueous phase by means of dialysis or precipitation with ethanol (Sambrook, J., Fritsch, E. F. and Maniatis, T., 1989, CSH, "Molecular Cloning").

These "traditional methods" for isolation of nucleic acids from cells and especially from tissues are very time-consuming (sometimes longer than 48 hours), require highly complex apparatus and beyond that are also not feasible under field conditions. Moreover, such methods are hazardous to health to a not inconsiderable degree because of the chemicals used, such as phenol and chloroform.

The next generation of methods for isolation of nucleic acids is based on a method for preparative and analytical purification of DNA fragments from agarose gels, developed and described for the first time by Vogelstein und Gillespie (Proc. Natl. Acad. Sci. USA, 1979, 76, 615-619). The method combines the dissolution of the agarose containing the DNA bands to be isolated in a saturated solution of a chaotropic salt (NaI), with binding of the DNA on glass particles. The DNA fixed on the glass particles is then washed with a washing solution (20 mM Tris HCl [pH 7.2]; 200 mM NaCl; 2 mM EDTA; 50% v/v ethanol) and then detached from the carrier particles. Heretofore this method has undergone a series of modifications and at present is applied for different methods of extraction and purification of nucleic acids from different sources, ultimately becoming the basis for almost all commercially available kits for manual and also automated isolation of nucleic acids. Furthermore, numerous patents and publications are now known that relate to the basic principle of isolation of nucleic acids published for the first time by Vogelstein and Gillespie, some of them containing further advantages. These variants concern both the use of different mineral carrier materials and the type of buffers used for binding the nucleic acids. Examples include the binding of nucleic acids on mineral carriers in the presence of solutions of different chaotropic salts, in which finely ground glass powder (BIO 101, La Jolla, Calif.), diatomaceous earths (Sigma Co.) or even silica gels or silica suspensions or glass-fiber filters or mineral ores (DE 4139 664 A1; U.S. Pat. No. 5,234,809; WO-A 9534569; DE 4321904: DE 20207793) are used as carrier materials. All of these specifications are based on the binding of nucleic acids on a mineral carrier material on the basis of glass or silicon in the presence of chaotropic salt solutions. In more recent patent specifications, it is disclosed that so-called anti-chaotropic salts as components of lysing/binding buffer systems can also be used very efficiently and successfully for adsorption of nucleic acids on the mineral materials known to and used by the person skilled in the art (EP 1135479).

In summary, the prior art may therefore be described to the effect that nucleic acids bind to mineral materials in the presence of buffers that contain chaotropic or anti-chaotropic salts or even in the presence of buffers that contain mixtures of chaotropic and anti-chaotropic salts, and in this way can then also be isolated. In this connection, preferred variants are also known in which aliphatic alcohols are additionally used for mediation of binding. It is also known to the person skilled in the art that all common commercial products for isolation and purification of nucleic acids are based on this principle. The mineral carriers, used for this purpose have the form of loose bulk material, the form of filter membranes or even the form of suspensions. Paramagnetic or magnetic particles are often used to perform automated extraction processes. Examples of these are silicate materials with a magnetic or paramagnetic core, or else iron oxide particles, the surface of which has been modified such that they have the functionalities necessary for binding nucleic acids. In this connection, the extraction sequences for isolation of nucleic acids are also based in principle on the same schemes; Lysis of the starting sample to liberate the nucleic acid, binding of the nucleic acid on the appropriate mineral carrier material, washing of the bound nucleic acid, drying of the carrier material and final elution of the bound nucleic acid from the carrier material. Even though these methods have proved useful, they nevertheless suffer from several disadvantages. For example, the binding capacity of the materials used is limited, especially in the case of use of spinfilter membranes. If the starting sample contains too much nucleic acid, membranes even become clogged in many cases. The automated process sequences using magnetic particles are relatively complex and, depending on application, are also relatively time-consuming. Simpler performance of nucleic acid isolation under field conditions is not feasible.

OBJECT OF THE INVENTION

The object underlying the invention was therefore to eliminate the disadvantages of the technical solutions described in the prior art.

ACHIEVEMENT OF THE OBJECT

The object has been achieved according to the features of the claims. According to claim 1, a method for isolation of nucleic acids from aqueous samples containing nucleic acids is described, wherein an aqueous solution that contains nucleic acids is free form or liberated by lysis is brought into contact, before or after the polarity of the aqueous solution is lowered, with a solid phase that has a rough or structured surface, whereupon the nucleic acids precipitate on the solid phase—and consequently become bound on the solid phase—and then, together with the solid phase, are removed from this aqueous solution. The phrase "before or after the polarity of the aqueous solution is lowered" describes both the possibility that the aqueous solution can first be brought into contact with the solid phase and then the polarity of the water lowered and also the possibility that the polarity of the water is first lowered and then contact with the solid phase is established. In the first cited option, precipitation of the nucleic acids on the soled phase takes place only when the polarity of the water is lowered—usually by addition of an alcohol. In the other variant, precipitation of the nucleic acids on the solid phase takes place immediately upon establishment of contact. If water-insoluble organic solvents are used, the mixture must be agitated in order for precipitation of the nucleic acids on the solid phase to take place. This is preferably achieved by moving the solid phase within the mixture.

Claims 2 to 13 show preferred embodiment of the claimed invention. Subject matter of the invention is also a test kit for performing the method as well as instruments therefor.

According to the invention, a method for isolation of nucleic acids has been provided which is much easier to perform than the known methods, which makes it possible to perform nucleic acid isolation even under field conditions (and by non-specialists), which can be performed extremely rapidly—especially in the contact of automated extraction—and which permits extremely high yields of nucleic acids with high quality to be isolated.

The invention was based on the following observation. If a sample containing nucleic acid is processed with extraction reagents of commercially available kits (e.g. innuPREP Blood DNA KIT/IPC16, Analytik Jena AG; D Neasy Blood & Tissue Kit; Qiagen Co.), and any appropriate plastic material with a rough surface (for exampled, roughened polypropylene) is used instead of a mineral carrier material and brought into contact with the sample being processed, nucleic acid binds on the plastic material.

The term "rough surface" is to be understood as a surface that is obviously not smooth to the touch or to the eye. However, it may also be a surface that has a structure (e.g. grooves). Because of this structure, the smoothness of the surface is eliminated, even if the structure, i.e. the grooves, may itself be smooth. According to the invention, such surfaces are referred to as "structured surfaces". If it is not obvious to the eye or to the touch whether a surface is smooth or rough, a test in which a laser beam is directed onto this surface may be performed. If the surface is smooth, the laser will be reflected only in the primary direction at the surface. In the case of rough surfaces, scattering takes place in all spatial directions. Such a test has been described on the website of Kiel University (http://www.tf.uni-kiel.de/matwis/amat/semitech_en/kap_3/illustr/oberflacchenstmkture.pdf) page 7.

The subsequent steps of washing can be performed with known alcohol-containing washing buffers or else merely with an alcohol; likewise, buffers of low salt concentration or even water may be used for elution. The only difference is that a rough plastic material is used instead of the mineral carrier material. As early as the first experiments, it was found that all process steps can be implemented much more easily and rapidly therewith. It is also evident that this effect could be observed with all rough plastic materials used. Initially, however, the special feature of all performed experiments was that the rough plastic materials used were produced on a 3D printer. Thereby the surface is not smooth but instead is rippled—in other words rough, since a body of layered structure is formed by 3D printing. These first experiments were performed using an automated extraction system (Thermo Electron), the so-called Kingfisher mL magnetic particle processor. This is an instrument for extraction of nucleic acids by means of magnetic particles. This instrument uses plastic combs, into which magnetic bars penetrate and then, in a walk-away process, move magnetic particles and are immersed in the buffers needed for standard extraction. These plastic combs were used outside their normal purpose to perform the inventive method. For this purpose, sleeves of various materials were printed by means of a 3D printer and then slipped onto the plastic combs. In each case, approx. $1\times10^6$ NIH 3T3 cells were used as the sample. By way of example, some of the reagents used for isolation of the nucleic acids were obtained from a commercially available extraction kit (innuPREP Blood DNA Mini Kit/IPC16; Analytik Jena AG). The extraction process took place as in the following workflow. Using the lysis buffer (Lysis Solution CBV) as well as Proteinase K, the cells were lysed at 60° C. for 15 minutes. During lysis, the reaction plastic of the Kingfisher mL was prefilled with the following solutions:

Cavity 1: 400 μL isopropanol
Cavity 2: 800 μL Washing Solution LS (from the extraction kit)
Cavity 3: 800 μL 80% ethanol
Cavity 4: 800 μL 80% ethanol
Cavity 5: 200 μL Elution buffer (from the extraction kit)

After lysis was performed, the lysate (400 μL) was added in cavity 1 to the isopropanol already present there and the extraction process was started. In this process, the plastic combs are moved successively from cavity 1 to cavity 5. In each cavity, the plastic combs are then made to move vertically in the respective buffer solution that is present. This extraction process is based on the traditional principles of nucleic acid isolation using magnetic particles. But no particles are used. In cavity 1, binding of the nucleic acid takes place on the plastic comb with the slipped-on sleeves. The bound nucleic acid is moved successively through cavities 2-4. The washing steps take place in these. They are followed by a brief drying step for removal of ethanol. Finally, the nucleic acid is detached from the plastic combs with sleeves in cavity 5. This process is greatly simplified, since no magnetic particles were processed. The necessary collection of magnetic particles is eliminated as a step, since no particles at all were used for extraction. Consequently, the method was completed in approximately 15 minutes. As already pointed out, it was found that nucleic acids can be isolated via binding to the plastic material used with all plastic materials used by employing commercially available extraction chemistry and following a standard extraction protocol. These observations were surprising. It was indeed known that biomolecules adsorb unspecifically on plastic materials, but do so from aqueous solutions in which they are present, and in any case only in extremely low quantities. Descriptions of how plastic materials can be used for isolation of nucleic acids are also known. However, this requires that the plastic materials be chemically modified on their surfaces such that they have the same functional groups as silicate materials (OH groups) or else such that other functional groups (COOH groups) have been synthesized on plastic surfaces. This is mentioned, for example, in patent specification EP 1135479. However, it is also known to the person skilled in the art that such means for isolation of nucleic acids have not proved useful in practice, since in particular the binding capacity is much too low. After these first experiments, it became possible to show that nucleic acids can be isolated with the printed plastic sleeves. Nevertheless, it was not evident why this is possible. Surprisingly, it was possible to find the explanation with a quite simple experiment. Once again, the KingFisher mL was used. However, no printed plastic sleeves were used is this experiment. The standard plastic combs used for magnetic particle processing were used. Some of these plastic combs were used as is, while other combs were roughened at the surface by means of an engraving machine. Extraction—as already described—was carried out from cells using the same described reagents and the same process. The detailed results are described in Exemplary Embodiment 1.

The experiment shows impressively that no nucleic acid binds to the untreated combs. In contrast, nucleic acid binds highly efficiently to the roughened combs. Consequently, it was possible to obtain proof that it is merely necessary to roughen the surface of plastic materials in order to isolate nucleic acids highly efficiently using standard extraction reagents. However, the experimental observations also suggest another interesting fact. In the first experiments, as already described, reagents from commercial kits were used for isolation of nucleic acids. Instead of the binding of nucleic acids to mineral solid phases (such as, for example, centrifugation-filter membranes or magnetic particles), isolation of the nucleic acids takes place by means of the inventive rough surfaces used. The reagents used in this connection were always lysis buffers in combination with a binding buffer, which was an alcohol. It is known that the lysis buffers are combinations of salts, wetting and dispersing agents, complexity agents and further components. These buffer compositions in combination with alcohols facilitate the known binding of nucleic acids on mineral materials. It has also been known for a very long time that high concentrations of chaotropic salts facilitate the binding of nucleic acids on mineral materials. It has been found, however, that, in the presence of aqueous solutions having a high concentration of a chaotropic salt, nucleic acids bind to a mineral material but not to a roughened plastic surface. This observation leads to the suspicion that the mechanism of isolation of nucleic acids by means of rough surfaces had to be different from the previously known or suspected mechanisms of binding of nucleic acids to mineral materials.

As is already known from the prior art, under traditional conditions, DNA is isolated from cells and tissues by digesting the starting materials containing nucleic acids under strongly denaturing and reducing conditions, sometimes also with use of protein-degrading enzymes, purifying the resulting nucleic acid fractions via phenol/chloroform extraction steps and obtaining the nucleic acids from the aqueous phase by means of dialysis or precipitation with ethanol. In this connection, it is known to the person skilled in the art that, at very high concentrations of high molecular weight DNA, and after precipitation with ethanol, DNA precipitates as "threads" and can be wound around a glass rod and removed from the reaction vessel. However, this works only at high concentrations of DNA and under the prerequisite that the DNA is also a high molecular weight molecule. In most cases, therefore, ethanol precipitation is based on centrifuging the sample after addition of alcohol and precipitating the DNA as pellets. If the DNA concentrations are low, the sample must then be additionally incubated for several hours at −20° C., before it can be centrifuged for precipitation of the nucleic acids. In these cases, the centrifugation time must then also be greatly prolonged and may require several hours. Thus the "winding" of a highly concentrated and high molecular weight DNA onto a glass rod represents a special case. This has certainly been known for decades, but it cannot be automated.

In contrast, the centrifugation-based precipitation of nucleic acids is time-consuming and likewise difficult to automate. For this reason, time proves really impressively that the further development of technologies for isolation and purification of nucleic acids in the prior art took place from the traditional methods up to binding of nucleic adds on mineral carrier materials. These technologies are implemented in a form in which a sample containing nucleic acid is bound by means of centrifugation or vacuum on a filter material or nucleic acids are bound on magnetic or paramagnetic particles by means of magnetic separation. As regards the inventive isolation of nucleic acids by means of "binding" on a rough surface, this appears to be based on the circumstance that, after the sample has been brought into contact with a rough surface, the nucleic acids contained in the sample precipitate on the rough surface. This is accomplished by adding, for example, an alcohol that lowers the polarity of the environment and in this way reduces the solubility of the nucleic acid. Surprisingly, the "precipitation" of the nuclear acids on a rough surface takes place extremely efficiently and thus also makes it possible to isolate samples with low concentrations of nucleic acids simply and rapidly in an automated process. No centrifugation steps are necessary for this purpose.

The core of the invention therefore consists in the fact that nucleic acids in free form or liberated by lysis are present in an aqueous environment, the polarity of which is adjusted in such a way by means of organic substances that the solubility of the nucleic acid is reduced, after which this aqueous environment is brought into contact with a rough surface, so that the nucleic acid then precipitates on the rough surface, after which the precipitated DNA is detached from the rough surface once again and becomes available. Optionally, the nucleic acid precipitated on the rough surface may also be washed and then detached after washing steps.

Thus the present invention makes it possible in the most ideal way to implement the already stated objective. The only requirements for extraction are a material, the surface of which has been roughened, and an aqueous environment in which the nucleic acid to be isolated is present, the conditions of which have been so adjusted by means of an organic substance that the solubility of the nucleic acid is reduced to the point that it precipitates on the rough surface. This precipitation on the rough surface takes place by bringing the rough surface into contact with the sample or by bringing the sample into contact with the rough surface. As an example, traditional kit reagants (e.g. lysis buffers) of different types may be used as extraction reagents. The necessary conditions for precipitation of nucleic acid on the rough surface are adjusted by addition of an organic substance. Likewise, the extraction protocol works according to the known scheme of lysing, binding, washing and elating. Alternatively, washing steps may also be omitted. Now, however, the method can be performed extremely easily and rapidly. It may be performed in the following steps:

1. Lysing of a sample containing nucleic acid (or preparation of a liquid sample containing nucleic acid). For lysis of a sample, a traditional lysis buffer or a buffer known previously from methods for isolation of nucleic acids is mixed with the sample. These buffers may contain chaotropic salts or non-chaotropic salts or mixtures of these two groups. Furthermore, these buffers may contain further components, such as chelating agents, Tris buffer, wetting and dispersing agents, etc. However, the method also functions with buffers that do not contain any salts and, for example, consist only of a detergent, Tris and EDTA. In addition, it is also still possible to use proteolytic enzymes.
2. Addition of a binding buffer, which contains an alcoholic component and further additives, or addition of an alcohol alone or even addition of acetone or petroleum ether.
3. Bringing this mixture into contact with a material, the surface of which is non-smooth. The surface may be rough or provided with a structure.
4. Removal of the rough or structured material together with the bound nucleic acid from the mixture, or removal of the mixture from the material
5. If necessary, washing of the material.
6. If necessary, drying of the material.
7. Detachment of the nucleic acid from the material with an elution buffer (buffer of low salt concentration, or water).

The method is universally usable and can be performed in an automated process as well as manually. Thus it is also most ideal for use of nucleic acid extraction under field conditions, since the necessary steps are easy to perform. The inventive materials to be used are likewise not limitative.

So-called composite materials, which represent mixtures of polymers and, for example, organic components or metallic components, may also be used. What is essential is merely the provision of a roughened surface or of a surface provided with a structure. The architecture of the inventive material is likewise not limitative. The use of rough, magnetic material is also advantageous. Such a material is known as granulated material under the brand name TECA-COPM®. For example, even a standard pipette tip can be roughened on its inside according to the invention and used manually or in an automated process for extraction of nucleic acids. For this purpose, the extraction protocol proceeds successively in conformity with the described extraction workflow, by means of multiple pipetting steps. Thus it is clear to the person skilled in the art how extremely easily extraction of nucleic acids can now be performed by means of the present invention. The present invention has one further enormous advantage. If a biological sample contains large quantities of nucleic acids, an extremely large quantity of nucleic acids can be extracted by means of the inventive method and the inventive plastic. The yields in this case are many times larger than the yields achievable with known extraction methods using mineral carrier materials. Thus the method is also ideally suited for processing of large sample volumes. It has also been found that not only genomic DNA and RNA but also plasmid DNA can be isolated. The inventive method can be processed extremely rapidly as an automated process of extraction of multiple samples. For example, 15 samples can be processed simultaneously in 15 minutes by means of the inventive method, using the KingFisher mL beyond its normal purpose. This method can even be further shortened without loss of quantity and quality of the nucleic acid to be isolated. This may then also be transferred to other automated stations. For example, the extraction may even be implemented in roughened pipette tips, using all common automated pipetting systems. The invention therefore makes available, for isolation and purification of nucleic acids, a completely new platform technology, which has a large number of quite obvious advantages compared with the known extraction methods. Subject matter of the invention is therefore also an instrument for isolation of nucleic acids, comprising roughened pipette tips.

The invention will be explained in more detail hereinafter on the basis of exemplary embodiments. These exemplary embodiments do not represent any limitation of the invention.

EXEMPLARY EMBODIMENTS

Example 1

Evidence of Binding of Nucleic Acids on Rough Surfaces Using Commercially Available Extraction Chemistry The evidence that nucleic acids can be bound on rough surfaces and isolated was obtained as follows. For this purpose, the extraction was implemented in an automated process. A magnetic particle processor (KingFisher mL; Thermo Electron) was used. This instrument uses plastic combs, into which magnetic bars penetrate and then, in a walk-away process, move magnetic particles, which are used for isolation of nucleic acids. These plastic combs were used outside their normal purpose to perform the inventive method, and they were expected to achieve binding and subsequent extraction of the nucleic acids. The plastic material is polypropylene. According to the present invention the plastic combs were roughened by means of a grinding machine. Unroughened plastic combs were likewise used. In each case, approx. $1 \times 10^6$ NIH 3T3 cells were used as the sample. The extraction chemistry used for isolation of the nucleic acids was obtained in part from the commercial extraction kit known as innuPREP Blood DNA Kit/IPC 16X (Analytik Jena AG). Using a lysis buffer (Lysis Solution CBV) as well as Proteinase K, the cells were lysed at 60° C. for 15 minutes. During lysis, the reaction plastic of the Kingfisher mL was filled with the following solutions:

Cavity 1: 480 µL isopropanol

Cavity 2: 800 µL Washing Solution LS (from the extraction kit)

Cavity 3: 800 µL 80% ethanol

Cavity 4: 800 µL 80% ethanol

Cavity 5: 200 µL Elution Buffer (from the extraction kit)

After lysis was performed, the lysate (400 µL) was added in cavity 1 to the isopropanol already present there and the extraction process was started. In this process, the plastic combs are moved successively from cavity 1 to cavity 5. In each cavity, the plastic combs are then made to move vertically in the respective buffer solution that is present. This extraction process is based on the traditional principles of nucleic acid isolation using magnetic particles. But no particles are used. In cavity 1, binding of the nucleic acid takes place on the plastic comb. The bound nucleic acid is moved successively through cavities 2-4. The washing steps take place in these. They are followed by a brief drying step for removal of ethanol. Finally, the nucleic acid is detached from the plastic combs in cavity 5. As already pointed out, plastic combs with roughened surface as well as the original untreated plastic combs were used. The isolated nucleic acid was detected by means of spectrophotometric measurement and also on agarose gel. Besides the yield, the parity of the isolated nucleic acid was also determined.

Results of the spectrophotometric measurement:

| Sample | Concentration (ng/μL) | Yield (μg) | Ratio $A_{260}$:$A_{280}$ | Ratio $A_{260}$:$A_{230}$ |
|---|---|---|---|---|
| untreated plastic comb 1 | 0 | not measurable | not measurable | not measurable |
| untreated plastic comb 2 | 0 | not measurable | not measurable | not measurable |
| roughened plastic comb 1 | 56 | 11.2 | 1.90 | 2.46 |
| roughened plastic comb 2 | 60 | 12 | 1.86 | 2.30 |
| roughened plastic comb 3 | 63 | 12.6 | 1.96 | 239 |

Figure 1:
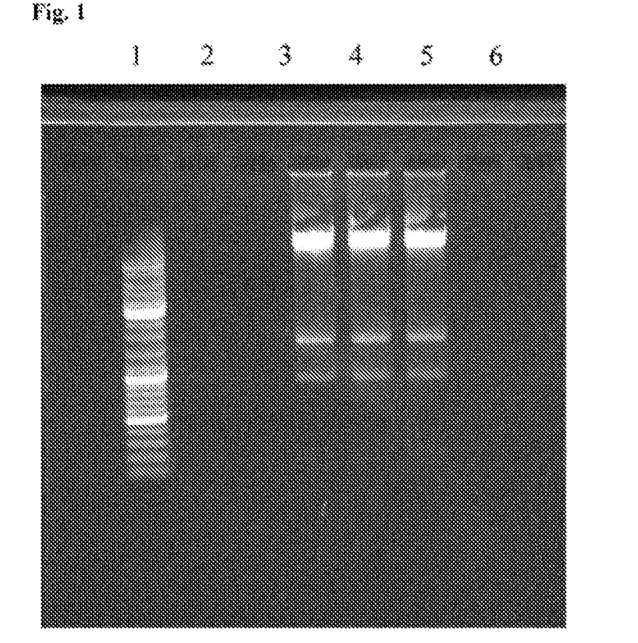
FIG. 1 shows the detection of DNA on an agarose gel in Example 1.

FIG. 1 shows the detection of DNA on an agarose gel. In each lane, 4 μL nucleic acid was used out of the total eluate of 200 μL. The lanes correspond to:
1. DNA ladder (1b ladder)
2. Untreated plastic comb
3. Untreated plastic comb
4. Roughened plastic comb 1
5. Roughened plastic comb 2
6. Roughened plastic comb 3

As the results impressively show, the nucleic acid (both DNA and RNA) does not bind to the untreated combs. However, it binds highly efficiently to the roughened combs and thereafter can be washed with traditional washing buffers and finally detached from the combs once again. Thus the process corresponds exactly to the traditional processes of isolation of nucleic acids by means of magnetic particles or by means of mineral carrier materials known to the person skilled in the art. However, the process can be carried out very much more rapidly and easily. With this example, it has therefore been demonstrated that, merely by roughening a plastic surface, this material can be used for extraction of nucleic acids with known extraction reagents.

Example 2

Testing of Different Plastic Materials with Rough Surfaces for the Extraction of Nucleic Acids using Commercially Available Extraction Chemistry The evidence that nucleic acids can be bound on rough surfaces of different plastic materials and isolated was obtained as follows. For this purpose, the extraction was implemented in an automated process. Once again, the KingFisher mL magnetic particle processor was used. The plastic combs were used outside their normal purpose to perform the inventive method. A plastic comb roughened as in Exemplary Embodiment 1 was used as the material for binding the nucleic acid. An untreated comb was used as the control. For testing of other materials, plastic rings of different materials were made by means of a 3-D printer and in turn were slipped onto the combs of the KingFisher mL instrument. These rings also were once again roughened with a grinding machine. The different materials were roughened combs of the plastic of the KingFisher mL (polypropylene); furthermore, the material Biofila Linen (TwoBEars Co.), a composite material consisting of lignin and a complex polymer of aromatic alcohols, the material acrylonitrile-butadiene-styrene (ABS), the material from polylactite (PLA), the material polycarbonate (PC) and the material polystyrene (PS). For this purpose, the combs of the KingFisher mL were roughened in different ways (type A: approx. 3 cm of the comb, type B: approx. 1 cm of the comb; C. only the tips of the comb). In each case, approx. $1 \times 10^6$ NIH 3T3 cells were used as the sample. The extraction chemistry used for isolation of the nucleic acids was again obtained in part from the commercial extraction kit known as innuPREP Blood DNA Kit/IPC 16 (Analytik Jena AG). Using a lysis buffer (Lysis Solution CBV) as well as Proteinase K, the cells were lysed at 60° C. for 15 minutes. During lysis, the reaction plastic of the KingFisher mL was filled with the following solutions:
Cavity 1: 400 μL isopropanol
Cavity 2: 800 μL Washing Solution LS (from the extraction kit)
Cavity 3: 800 μL 80% ethanol
Cavity 4: 800 μL 80% ethanol
Cavity 5: 200 μL Elution Buffer (from the extraction kit)

After lysis was performed, the lysate (400 μL) was added in cavity 1 to the isopropanol already present there and the extraction process was started. The extraction process was earned out as described in Exemplary Embodiment 1. The plastic combs (untreated and roughened respectively) as well as the plastic combs with the slipped-on plastic rings were again moved successively through the individual cavities containing the previously introduced buffer solutions. Finally, the nucleic acid was detached from the plastic combs in cavity 5. The isolated nucleic acid was detected by means of spectrophotometry measurement and also on agarose gel. Besides the concentration and yield, the purity of the isolated nucleic acid was also determined.

Results of the spectrophotometry measurement:

| Sample | Concentration (ng/μL) | Yield (μg) | Ratio $A_{260}$:$A_{280}$ | Ratio $A_{260}$:$A_{230}$ |
|---|---|---|---|---|
| untreated plastic comb | No nucleic acid measurable | not determinable | not determinable | not determinable |
| roughened plastic comb type A | 84 | 16.8 | 1.91 | 1.98 |
| roughened plastic comb type B | 95 | 19 | 1.92 | 2.01 |
| roughened plastic comb type C | 75 | 15 | 1.90 | 2.11 |
| Plastic comb with roughened ring of BioFila | 178 | 35.6 | 1.95 | 2.22 |
| Plastic comb with roughened ring of ABS | 179 | 35.8 | 2.03 | 2.30 |
| Plastic comb with roughened ring of PLA | 205 | 41 | 1.94 | 1.98 |
| Plastic comb with roughened ring of PC | 185 | 37 | 1.99 | 2.28 |
| Plastic comb with roughened ring of PS | 157 | 31.4 | 1.96 | 2.32 |

Figure 2:
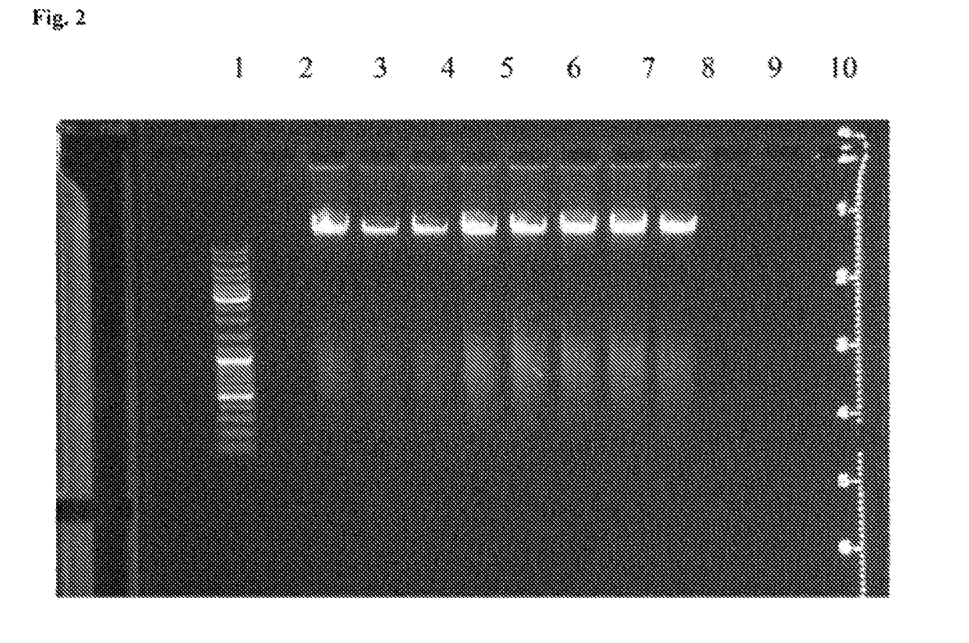
FIG. 2 shows the detection of DNA on an agarose gel in Example 2.

FIG. 2 shows the detection of DNA on an agarose gel. In each lane, 4 μL nucleic acid was used out of the total eluate of 200 μL. The lanes show:
1. DNA ladder (1b ladder)
2. Untreated plastic comb
3. Roughened plastic comb type A
4. Roughened plastic comb type B
5. Roughened plastic comb type C
6. Plastic comb with roughened ring of BioFila
7. Plastic comb with roughened ring of ABS
8. Plastic comb with roughened ring of PLA
9. Plastic comb with roughened ring of PC
10. Plastic comb with roughened ring of PS As the results show, the nucleic acid does not bind to the untreated combs. However, it binds highly efficiently to the roughened combs and the roughened rings. Thus it is demonstrated that the binding is independent of the type of material. All roughened materials bind nucleic acids highly efficiently. It is likewise demonstrated that the roughened face (in the case of the combs) even only has to be very small in order to bind nucleic acids. It is also demonstrated, however, that larger faces also bind even greater quantities of nucleic acids (the faces of the rings being used are larger than the roughened surfaces of the combs). The quality of the nucleic acids is excellent Example 3

Comparison of a Traditional Kit for Isolation of Nucleic Acids with the Inventive Method With this example it was intended to draw a comparison between a traditional kit for isolation of nucleic acids and the inventive method. The DNeasy Blood & Tissue Kit of the Qiagen Co. was used as the comparison kit. This is based on lysis of the cells, binding of the nucleic acids to the surface of a spinfilter column containing a silica membrane, subsequent washing of the bound nucleic acid and final elution of the nucleic acid from the silica membrane. This kit is a standard kit for extraction of nucleic acids and is used throughout the world for this purpose. The process was carried out according to the current manual.

Once again the Kingfisher mL was used to perform the inventive method. A roughened comb and a ring of roughened PLA slipped onto the comb were used as the rough surface. The process of extraction by means of the inventive method was carried out as described in both Exemplary Embodiments 1 and 2. In each case, approx. $1 \times 10^6$ NIH 3T3 cells or $2 \times 10^6$ NIH 3T3 cells were used as the sample. The isolated nucleic acid was detected by means of spectrophotometric measurement and also on agarose gel. Besides the concentration and yield, the purity of the isolated nucleic acid was also determined.

Results of the spectrophotometric measurement:

| Sample | Concentration (ng/µL) | Yield (µg) | Ratio $A_{260}$:$A_{280}$ | Ratio $A_{260}$:$A_{230}$ |
|---|---|---|---|---|
| Qiagen Kit ($1 \times 10^6$ cells) | 49 | 9.8 | 1.88 | 2.15 |
| Qiagen Kit ($2 \times 10^6$ cells) | 57 | 11.4 | 1.84 | 2.21 |
| Roughened plastic comb ($1 \times 10^6$ cells) | 101 | 20.2 | 1.87 | 2.04 |
| Roughened plastic comb ($2 \times 10^6$ cells) | 147 | 29.4 | 1.98 | 2.15 |
| Plastic comb with roughened ring of PLA ($1 \times 10^6$ cells) | 240 | 48 | 1.96 | 2.20 |
| Plastic comb with roughened ring of PLA ($2 \times 10^6$ cells) | 503 | 100.6 | 1.96 | 2.20 |

Figure 3:
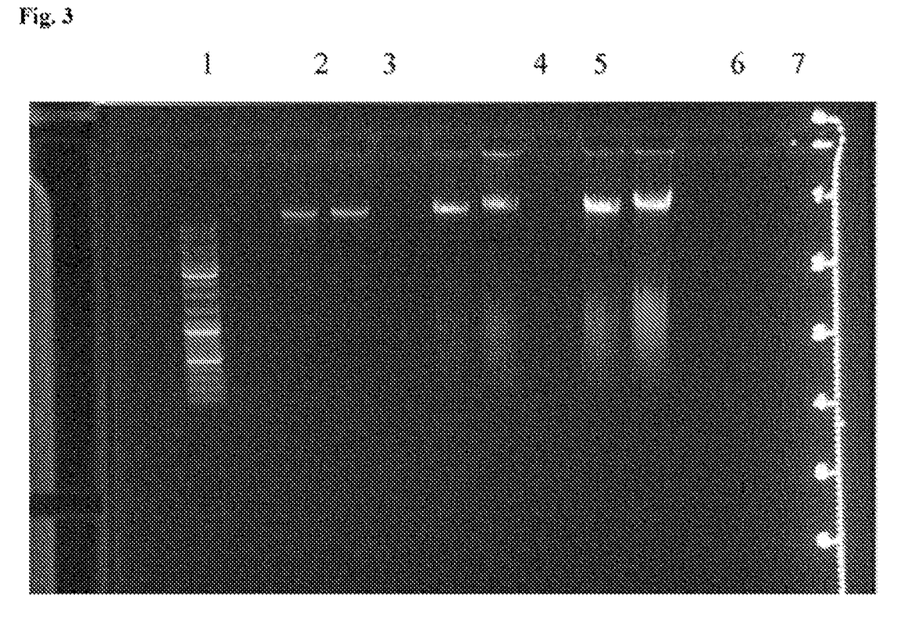
FIG. 3 shows the detection of DNA on an agarose gel in Example 3.

FIG. 3 shows the detection of DNA on an agarose gel. In each lane, 2 µL nucleic acid was used out of the total eluate of 200 µL. The lanes show:
1. DNA ladder (1b ladder)
2. Qiagen Kit (approx. $1 \times 10^6$ cells)
3. Qiagen Kit (approx. $2 \times 10^6$ cells)
4. Inventive method; Roughened plastic comb (approx. $1 \times 10^6$ cells)
5. Inventive method; Roughened plastic comb (approx. $2 \times 10^6$ cells)
6. Inventive method; plastic comb with roughened ring of PLA (approx. $1 \times 10^6$ cells)
7. Inventive method; plastic comb with roughened ring of PLA (approx. $2 \times 10^6$ cells)

As the results show, a very much larger quantity of nucleic acids can be bound and isolated with the inventive method than with a traditional kit. Thus the binding capacities are much higher than the binding capacities of a commercially available silica-membrane method. This highlights the enormous advantage of the inventive method.

Example 4

Extraction of Nucleic Acids from Blood

With this example it is demonstrated that, by means of the inventive method, DNA can also be isolated from blood samples and at the same time the yields are extremely high. 3-mL samples of whole blood were used. After lysis of the erythrocytes, the nucleated cells were pelletized and, once again after addition of a lysis buffer (lysis buffer CBV) from the commercially available kit innuPREP Blood DNA Kit/IPC16 (Analytik Jena AG) as well as addition of Proteinase K, were lysed at 60° C. for 30 minutes. Elution was carried out in 300 µL Elution Buffer.

Once again the Kingfisher mL was used to perform the inventive method. Rings of roughened BioFila as well as PLA material slipped onto the comb were used as the rough surfaces. The process of extraction by means of the inventive method was carried out as described in Exemplary Embodiments 1 to 3.

The isolated nucleic acid was detected by means of spectrophotometric measurement Results of the spectrophotometric measurement:

| Sample | Concentration (ng/µL) | Yield (µg) | Ratio $A_{260}$:$A_{280}$ | Ratio $A_{260}$:$A_{230}$ |
|---|---|---|---|---|
| Plastic comb with roughened ring of Biofila | 270 | 81 | 1.78 | 2.22 |
| Plastic comb with roughened ring of PLA | 306 | 91.8 | 1.80 | 2.22 |

As the results show, it is possible with the inventive method to isolate nucleic acids even from samples of whole blood, in which case the attainable yields are extremely high.

Example 5

Extraction of Nucleic Acid from NIH 3T3 Cells as Well as from Samples of Whole Blood by Means of the Inventive Method Using a Modified Pipette Tip With this example it is demonstrated that, by means of the inventive method, nucleic acids can be isolated extremely easily and rapidly by means of a modified pipette tip.

A 1-mL pipette tip of the Sarstedt Co. was used as the pipette tip. This pipette tip was shortened by approx. 5 cm. In conformity with the inventive method, the inside of the pipette tip was then roughened by means of a grinding machine.

$1 \times 10^6$ NIH 3T3 cells as well as 2 mL whole blood were used (the erythrocytes were lysed and the nucleated cells were pelletized, and these cells were then used). Both the cells and the pelletized nucleated blood cells were treated as in the preceding exemplary embodiments and lysed with lysis buffer CSV. The lysate was transferred into a 2-mL reaction vessel and 400 μL isopropanol was mixed therewith. Then the roughened pipette tip was used, and the mixture was filled into and emptied from a pipette 20 times. Thereafter 3 further 2-mL reaction vessels were filled with the known alcoholic washing buffers (LS, 80% ethanol, 80% ethanol). The pipette tip was then immersed successively in the respective washing buffer and the pipette was filled and emptied 5 times in each case. After the last washing step, the tip was dried, so that the remaining ethanol was removed. The bound nucleic acid, was eluted with 200 μL Elution Buffer for the NIH 3T3 cells as well as with 400 μL for the whole blood sample. It was again introduced into a 2-mL reaction vessel. This was emptied and refilled 20 times by pipette. After removal of the pipette tip, the isolated nucleic acid was contained in the reaction vessel. The method is extremely easy and fast.

The isolated nucleic acid was detected by means of spectrophotometry measurement.

Results of the spectrophotometric measurement:

| Sample | Concentration (ng/μL) | Yield (μg) | Ratio $A_{260}:A_{280}$ | Ratio $A_{260}:A_{230}$ |
|---|---|---|---|---|
| approx. 1 × 10⁶ NIH 3T3 cells, untreated pipette tip | No nucleic acid measurable | not determinable | not determinable | not determinable |
| approx. 1 × 10⁶ NIH 3T3 cells, roughened pipette tip | 84 | 16.8 | 1.97 | 1.88 |
| 2 mL whole blood (lymphocyte pellet); Untreated pipette tip | no nucleic acid measurable | not determinable | not determinable | not determinable |
| 2 mL whole blood (lymphocyte pellet); Roughened pipette tip | 235 | 94.0 | 1.79 | 2.17 |

As the results show, it is possible with the inventive method, solely by using a pipette tip, the inside of which has been roughened according to the invention, to bind and to isolate nucleic acids. Here also it has been found that the yields are extremely high. No nucleic acids can be isolated by means of the untreated pipette tip.

Example 6

Testing of Different Lysis Buffers in Combination with Different Alcoholic or Non-alcoholic Solutions for Extraction of Nucleic Acids by Means of the Inventive Method Once again the KingFisher mL magnetic particle processor was used. A roughened ring of BioFila material, roughened with a grinding machine and slipped onto the combs of the plastic of the KingFisher mL, was used as the material for binding the nucleic acid. In each case, approx. 1×10⁶ NIH 3T3 cells were used as the sample. Lysis of the cells was carried out with three different buffers:
1. Buffer A, containing a chaotropic salt; urea, SDS, Tris HCl, EDTA
2. Buffer B, containing no salt: SDS; Tris HCl; EDTA
3. Buffer C containing a non-chaotropic salt: sodium, chloride, CTAB; Tris HCl, EDTA The cells were resuspended in 200 μL H₂O, 200 μL of the respective lysis buffer as well as 20 μL was mixed therewith, and the cells were lysed at 60° C. for 15 minutes. During lysis, the reaction plastic of the Kingfisher mL was filled with the following solutions:
Cavity 1: 400 μL isopropanol or absolute ethanol or acetone
Cavity 2: 800 μL Washing Solution LS (from the extraction kit innuPREP Blood DNA Kit/IPC16)
Cavity 3: 800 μL 80% ethanol
Cavity 4: 800 μL 80% ethanol
Cavity 5: 200 μL Elution Buffer (from the extraction kit innuPREP Blood DNA Kit/IPC16)

After lysis was performed, the lysate (400 μL) was added in cavity 1 to various solutions already present there (isopropanol absolute ethanol and acetone) and the extraction process was started. The extraction process was earned out as described in Exemplary Embodiment 1. The isolated nucleic acid was detected by means of spectrophotometry measurement and also on agarose gel. Besides concentration and yield, the parity of the isolated nucleic acid was also determined.

Results of the spectrophotometric measurement:

| Sample | Concentration (ng/μL) | Yield (μg) | Ratio $A_{260}:A_{280}$ | Ratio $A_{260}:A_{230}$ |
|---|---|---|---|---|
| Lysis buffer A + isopropanol | 174 | 34.8 | 1.90 | 2.10 |
| Lysis buffer A + abs. ethanol | 213 | 42.6 | 1.89 | 2.11 |
| Lysis buffer A + acetone | 220 | 44 | 1.92 | 2.17 |
| Lysis buffer B + isopropanol | 150 | 30 | 1.90 | 2.11 |
| Lysis buffer B + abs. ethanol | 106 | 21.2 | 1.80 | 1.99 |
| Lysis buffer B + acetone | 128 | 25.6 | 1.87 | 1.97 |
| Lysis buffer C + isopropanol | 112 | 22.4 | 1.85 | 1.97 |
| Lysis buffer C + abs. ethanol | 98 | 19.6 | 1.86 | 2.00 |
| Lysis buffer C + acetone | 89 | 17.8 | 1.87 | 1.99 |

Figure 4:
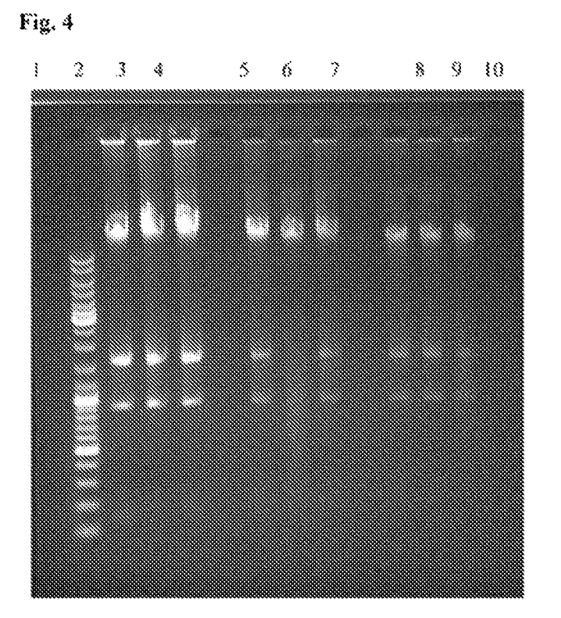
FIG. 4 shows the detection of DNA on an agarose gel in Example 6.

FIG. 4 shows the detection of DNA on an agarose gel. In each lane, 4 μL nucleic acid was used out of the total eluate of 200 μL. The lanes show:
1. DNA ladder (1b ladder)
2. Lysis buffer A+isopropanol
3. Lysis buffer A+abs. ethanol
4. Lysis buffer A+acetone
5. Lysis buffer B+isopropanol
6. Lysis buffer B+abs. ethanol
7. Lysis buffer B+acetone
8. Lysis buffer C+isopropanol
9. Lysis buffer C+abs. ethanol
10. Lysis buffer C+acetone As the results show, lysis buffers of different compositions as well as combinations of these lysis buffers with alcohols or even with a non-alcohol can be used for the inventive method. In this connection, chaotropic salts, no salt or else non-chaotropic salts may be present in the lysis buffer.

Example 7

Evidence of Recovery of Genomic DNA from an Aqueous Solution

An aqueous solution containing genomic DNA isolated from blood was prepared, 30 μL of a 3-molar sodium acetate solution as well as 300 μL isopropanol was mixed with 300 μL of this DNA solution.

The evidence that nucleic acids already well isolated can also be bound on rough surfaces and isolated was obtained as follows. For this purpose, the extraction was implemented in an automated process. Once again the KingFisher mL was used to perform the inventive method. A ring of roughened Biofila material slipped onto the comb was used as the rough surface. This ring was made by means of 3-D printing technology and bad a riffled structure on the surface.

The reaction plastic of the Kingfisher mL was filled with the following solutions:
Cavity 1: DNA solution/sodium acetate/isopropanol
Cavity 2: 800 µL 80% ethanol
Cavity 3: empty
Cavity 4: empty
Cavity 5: 150 µL water The extraction process was carried out as described in Exemplary Embodiment 1, but this time only one washing step was performed. The isolated nucleic acid was detected on an agarose gel.

Figure 5:
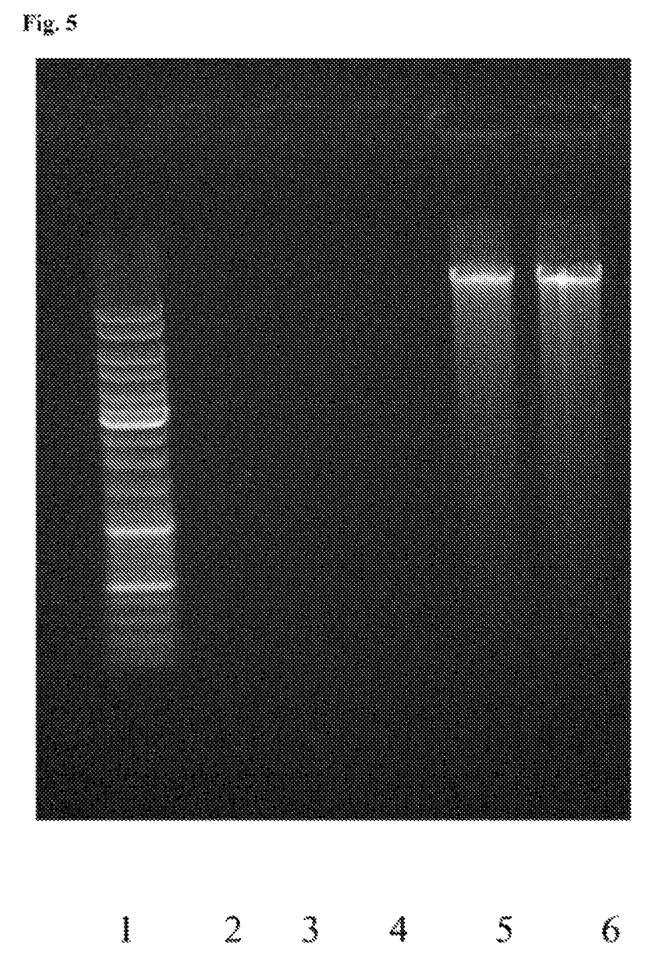
FIG. 5 shows the detection of DNA on an agarose gel in Example 7.

FIG. 5 shows the detection of DNA on an agarose gel. In each lane, 10 µL nucleic acid was used out of the total eluate of 150 µL. The lanes correspond to:
1. DNA ladder (1b ladder)
2. Empty
3. Untreated plastic comb
4. Untreated plastic comb
5. Plastic comb with slipped-on ring of Biofila and riffled structure
6. Plastic comb with slipped-on ring of Biofila and riffled structure As the results impressively show, the nucleic acid does not bind to the untreated combs. However, it binds to the rings that have riffled structure. In this way it has been proved that already existing DNA can also be recovered from an aqueous solution. The solubility of the DNA was lowered by the addition of isopropanol and sodium acetate, so that it was able to bind to the surface of the plastic material.

The invention claimed is:

1. A method for isolation of a nucleic acid from an aqueous sample that comprises a nucleic acid, the method comprising:
   contacting an aqueous solution that comprises a nucleic acid in free form or liberated by lysis with a solid phase that has a rough or structured surface;
   lowering the polarity of the aqueous solution before or after said contacting;
   whereupon said contacting, precipitating the nucleic acid on the solid phase; and, thereafter,
   removing the precipitated nucleic acid together with the solid phase from the aqueous solution.

2. The method according to claim 1, wherein
   the nucleic acid comprises a short-chain and a long-chain nucleic acid, which bind simultaneously on the solid phase.
3. The method according to claim 1, wherein
   said lowering is carried out with an organic solvent, thereby
   lowering the polarity of the aqueous solution.
4. The method according to claim 3, wherein
   the organic solvent is present, during said lowering, in an amount of from 5 vol % and 90 vol %.
5. The method according to claim 1, wherein
   the aqueous solution further comprises at least one of:
   a) a salt;
   b) at least one detergent;
   c) an amino alcohol or a substance for adjustment of the pH.
6. The method according to claim 5, wherein
   a) the salt is present in a concentration of from 1 mM and 5 M,
   b) the detergent is present in a concentration of from 0.1 vol % and 30 vol %,
   c) wherein when an amino alcohol or substance is present, TRIS is present in a concentration of from 1 mM and 2 M.
7. The method according to claim 1, wherein
   the aqueous solution further comprises an additional additive.
8. The method according to claim 1, wherein
   the rough or structured surface is a non-smooth metal, plastic or rubber surface or magnetic particles.
9. The method according to claim 8, wherein
   the non-smooth surface is produced by 3D printing or by roughening a plastic.
10. The method according to claim 1, wherein
    the solid phase comprises a rough composite material.
11. The method according to claim 1, wherein
    the solid phase comprises a roughened pipette tip.
12. The method according to claim 1, wherein
    the solid phase with a structure surface is the thread of a screw, a metal sponge or granules, a twisted material or a 2- or 3-dimensional network structure.
13. The method according to claim 1, further comprising:
    moving the solid phase in the aqueous solution.
14. A test kit for isolation of a nucleic acid from an aqueous sample comprising a nucleic acid, the test kit comprising:
    at least one substance for lowering the polarity of the aqueous solution,
    at least one solid phase with a rough or structured surface for binding the nucleic acid, and
    an elution buffer.
15. The method according to claim 1, wherein said solid phase has a structured surface which has grooves.

* * * * *